United States Patent
Reiner et al.

[11] Patent Number: 5,711,961
[45] Date of Patent: Jan. 27, 1998

[54] PHARMACEUTICAL COMPOSITIONS BASED ON CHEWING GUM AND A METHOD FOR THE PREPARATION THEREOF

[75] Inventors: Alberto Reiner, Como; Alessandro Seneci, Milan, both of Italy

[73] Assignee: APR Applied Pharma Research S.A., Stabio, Switzerland

[21] Appl. No.: 619,459

[22] PCT Filed: Jul. 15, 1995

[86] PCT No.: PCT/EP95/02816

§ 371 Date: May 29, 1996

§ 102(e) Date: May 29, 1996

[87] PCT Pub. No.: WO96/03111

PCT Pub. Date: Feb. 8, 1996

[30] Foreign Application Priority Data

Jul. 26, 1994 [IT] Italy ............... MI94A1586

[51] Int. Cl.$^6$ ............................................. A61K 9/68
[52] U.S. Cl. ........................ 424/441; 424/440; 426/5; 426/3
[58] Field of Search ..................... 424/440, 441; 426/5, 3

[56] References Cited

U.S. PATENT DOCUMENTS

| | | | |
|---|---|---|---|
| 3,826,847 | 7/1974 | Ogawa | 426/3 |
| 4,238,510 | 12/1980 | Cherukuri et al. | 426/5 |
| 4,452,821 | 6/1984 | Gergely | 426/5 |
| 4,792,453 | 12/1988 | Reed | 426/5 |
| 4,929,447 | 5/1990 | Yang | 424/440 |
| 5,458,890 | 10/1995 | Williford | 426/3 |

FOREIGN PATENT DOCUMENTS 0 551 700 A1  7/1993  European Pat. Off. .

Primary Examiner—Thurman K. Page
Assistant Examiner—D. Faulkner
Attorney, Agent, or Firm—Nixon & Vanderhye

[57] ABSTRACT

Chewing gum tablets and their methods of preparation are disclosed. The gum tablets contain a mixture of chewing gum base and sugary microgranules with an additive agent and an active ingredient adsorbed onto their surface. A lacquer coating on the tablet contains cellulose and polyethlene glycols. The sugary microgranules are delayed release coated particles. The chewing gums act as vehicles for active ingredients. These active ingredients may be used alone or in combination in normal physical form in the form of coated microspheres.

43 Claims, No Drawings

PHARMACEUTICAL COMPOSITIONS BASED ON CHEWING GUM AND A METHOD FOR THE PREPARATION THEREOF

This application is a 371 of PCT/EP95/02816 Jul. 15, 1995.

The subject of the present invention is the preparation of chewing gums which act as vehicles for active ingredients. These active ingredients may be used alone or in combination, in their normal physical form or in the form of coated microspheres.

In a gum there may therefore be various combinations of an active ingredient in its physical form and of the same active ingredient converted into coated microspheres, in various ratios.

More specifically, the subject of the invention is the use of a particular lacquering system which enables the drug to be administered more effectively.

It should be borne in mind that an essential feature of the administration of active ingredients is that they should have a palatable taste since they are released during the progressive chewing of the gum.

For drugs which are bitter or have little taste but nevertheless have very rapid release kinetics, tests have therefore also been carried out on coating them with the use of the microencapsulation technique; according to the particular kinetic results to be achieved, sometimes, the microencapsulation technique was not used on the whole of the active ingredient under investigation but only on some of it in order to keep a proportion for immediate action and the rest for delayed action.

By way of non-limiting example, this technology is effective for drugs such as dimenhydrinate, the effect of which against nausea generally needs to be developed rapidly for a certain proportion and then to continue for as long as possible in the bloodstream. The same result is sought in analgesic, antipyretic, cough-suppressant and antihistamine drugs, etc.

This expedient also sometimes entirely eliminates the side effects of some active ingredients on palatability, the use of this technology simultaneously achieving two quite separate objects.

Chewing gum preparations are particularly acceptable to children who can ingest drugs with a pleasant taste with the use of a more congenial form of ingestion closer to a normal sweet.

Moreover, for active ingredients which are easily oxidisable, degradable or hygroscopic, certain coatings are used to stabilize them during the steps of the process to which they are subjected, ensuring that they are preserved better over time.

The present invention achieves the objects set with the use of two distinct features, that is, the use of active ingredients as they are, as microencapsulated powders, or coated, mixed with one another in various ratios, and the lacquering of the finished pharmaceutical form.

The technology used for the preparation of the gums indicated is described in broad terms, by way of non-limiting example, below.

STEP 1

The gum is sold in pellets which, in order to be easily workable and thus to be mixed with other components, are frozen to a temperature of between −20° C. and −25° C. in a suitable chamber.

This step enables the gum to be processed without problems like any raw chemical product presented as a non-homogeneous powder.

In fact frozen gum is easily ground with a Danioni mill to produce a fairly homogeneous granulate generally with a particle size of between 190 and 60 mesh.

The granulate thus obtained:

1) can be mixed easily with the bases used as sweeteners in a suitable 4-way rotary-blade or screw mixer in proportions of ⅓ of gum and ⅔ of sweet base up to ⅘ of gum and ⅕ of sweet base; the sweet base is produced with sugars such as dextrose, glucose, sucrose, invert sugar, fructose, mannose, or maltose, or with polyalcohols used as sweeteners such as sorbitol, maltitol, xylitol or marmitol, or with synthetic sweeteners such as saccharine, acesulfame or aspartame, as well as with mixtures of any of the sweeteners mentioned above in various proportions to produce a palatable finished product with an acceptable taste;

2) after it has been mixed with the sweetening components, it can be granulated moist and dried on a fluid bed.

STEP 2

The mixture obtained in point 1) or the granulate obtained in point 2) is supplemented with a lubricant such as Na or Mg/Ca stearate in a proportion generally of between 0.2% and 2%, or with stearic acid or hydrogenated vegetable oils or other lubricants permitted by the pharmaceutical regulations (such as hydrogenated castor oil or palm butter). For some preparations, it is sometimes also appropriate to use additives such as microgranular cellulose in quantities of between 0.1 and 2% and between 0.05 and 1% of precipitated silica.

The mixture as produced above can proceed to the flavouring stage with the use of flavourings in either liquid or powder form.

After the addition of the active ingredient or ingredients, as they are or wholly or partially coated, the whole mixture is then compressed with a rotary press provided with suitable punches which should be polished, chrome-plated or Teflon-coated.

The tablets thus produced are ready to be film-coated as if they were normal tablets containing active ingredients. The gum tablets are placed in a heated vessel with blown hot air, with spraying equipment, and with forced extraction.

The gum tablets are thus spray-lacquered with the use of lacquers usually prepared with suitable mixtures based on hydroxypropylmethyl cellulose, polyethylene glycol 6000, polyethylene glycol 400 and pigments, all dispersed in demineralized water or in solvents formed by alcohol/water or acetone/alcohol/water mixtures. The gum tablets, which are put back in a vessel, are lacquered with lacquers thus formed, at a working temperature which may vary between 30° C. and 40° C.

Alternatively, alcoholic, aqueous-alcoholic or acetonic shellac lacquers of other cellulose derivatives such as hydroxypropyl cellulose, methyl cellulose, ethyl cellulose, cellulose acetophthalate, carboxymethyl cellulose, hydroxyethyl cellulose, methylhydroxyethyl cellulose, or methylhydroxypropyl cellulose phthalate may be used for coating the gum tablets.

The gums in tablet form are then polished with carnauba wax and packed in suitable "blister" packs.

The technology described above produces finished products of palatable drugs such as vitamins and antihistamines, anti-inflammatories, dental products, products for the treatment of the main respiratory tracts, etc.

Stability tests have shown the drugs used to be very stable both from the point of view of protection against physical agents such as oxygen and moisture and as regards resistance to the effects of heat and light.

For some drugs, optimal kinetic curves have been obtained precisely with the use of this technology and with the use of a portion of the normal product combined with a portion of the microencapsulated product. Some examples of gum compositions are given purely by way of example:

| 1. VITAMIN C - 1.5 g of gum containing 250 mg of Vitamin C. | |
|---|---|
| Gum base | 0.800 g |
| Sorbitol | 0.400 g |
| Vitamin C, 98% coated | 0.250 g |
| Aspartame | 0.010 g |
| Flavourings | 0.015 g |
| Magnesium stearate | 0.015 g |
| Hydroxypropylmethyl cellulose | 0.008 g |
| Colourings | 0.002 g |
| Distilled water | 0.090 g |

| 2. TRICLOSAN 1.4 g of gum containing 0.010 mg of Triclosan | |
|---|---|
| Gum base | 0.850 |
| Sorbitol | 0.410 g |
| Triclosan | 0.00001 g |
| Aspartame | 0.09999 g |
| Flavourings | 0.015 g |
| Magnesium stearate | 0.015 g |
| Hydroxypropylmethyl cellulose | 0.008 g |
| Colourings | 0.002 g |
| Distilled water | 0.090 g |

| 3. CETYL PYRIDINIUM - 1.5 g of gum containing 1 mg of cetyl pyridinium | |
|---|---|
| Gum base | 0.950 g |
| Sorbitol | 0.500 g |
| Cetyl pyridinium | 0.001 g |
| Aspartame | 0.010 g |
| Flavourings | 0.014 g |
| Magnesium stearate | 0.015 g |
| Hydroxypropylmethyl cellulose | 0.008 g |
| Colourings | 0.002 g |
| Distilled water | 0.090 g |

| 4. DIMENHYDRINATE - 1.5 g of gum containing 25 mg of dimenhydrinate | |
|---|---|
| Gum base | 0.950 g |
| Sorbitol | 0.475 g |
| Dimenhydrinate, 50% microspheres | 0.036 g |
| Dimenhydrinate, normal | 0.007 g |
| Aspartame | 0.010 g |
| Flavourings | 0.015 g |
| Magnesium stearate | 0.015 g |
| Hydroxypropylmethyl cellulose | 0.008 g |
| Colourings | 0.002 g |
| Distilled water | 0.090 g |

| 5. CAMOMILE - 1.5 g of gum containing 250 mg of extract of camomile. | |
|---|---|
| Gum base | 0.800 g |
| Sorbitol | 0.415 g |
| Camomile extract | 0.250 g |
| Aspartame | 0.010 g |
| Magnesium stearate | 0.015 g |
| Hydroxypropylmethyl cellulose | 0.008 g |
| Colourings | 0.002 g |
| Distilled water | 0.090 g |

| 6. ASPIRIN - 1.5 g of gum containing 300 mg of aspirin | |
|---|---|
| Gum base | 0.750 g |
| Sorbitol | 0.400 g |
| Aspirin | 0.300 g |
| Aspartame | 0.010 g |
| Flavourings | 0.015 g |
| Magnesium stearate | 0.015 g |
| Hydroxypropylmethyl cellulose | 0.008 g |
| Colourings | 0.002 g |
| Distilled water | 0.090 g |

| 7. B-CAROTENE + VITAMIN E - 1.5 g of gum containing 25 mg of vitamin E and 50 mg of B-carotene | |
|---|---|
| Gum base | 0.850 g |
| Sorbitol | 0.500 g |
| Vitamin E, 50% coated | 0.050 g |
| β-carotene | 0.050 g |
| Aspartame | 0.010 g |
| Flavourings | 0.015 g |
| Magnesium stearate | 0.015 g |
| Hyroxypropylmethyl cellulose | 0.008 g |
| Colourings | 0.002 g |
| Distilled water | 0.090 g |

For slightly soluble active ingredients which nevertheless have moderate palatability, gum tablets which release the active ingredient immediately have been produced according to the formulations given below.

| 8. MEBENDAZOLE - 1.24 g gum tablet containing 200 mg of mebendazole | |
|---|---|
| Gum base | 474.8 mg |
| Sorbitol | 462.2 mg |
| Hydroxypropylmethyl cellulose | 23 mg |
| Glycerol | 21.6 mg |
| Menthol | 18.2 mg |
| Magnesium stearate | 12 mg |
| Aspartame | 8 mg |
| Essential oils of mint | 8 mg |
| Polyethylene glycol | 7 mg |
| Titanium dioxide | 5 mg |
| Quinoline yellow colouring | 0.2 mg |

| 9. SUCRALFATE - 1.5 g gum tablet containing 250 mg of sucralfate and possibly 100 mg of calcium carbonate | |
|---|---|
| Sorbitol | 587.600 mg |
| Gum base | 450 mg |
| Essential oil of mint | 24 mg |
| Menthol | 21 mg |
| Glycerol | 20 mg |
| Hydroxypropylmethyl cellulose | 12.875 mg |
| Magnesium stearate | 12 mg |
| Titanium dioxide | 12 mg |
| Polyethylene glycol | 5 mg |
| Aspartame | 4.400 mg |
| Anethole | 1 mg |
| Chlorophyll green | 0.125 mg |

In the case of unpalatable active ingredients such as Benzydamine (3 mg), Cimetidine (100 mg), Ibuprofen (200 mg), Nimesulide (50 mg), etc., sugary microgranules are prepared and the various active ingredients subsequently to be mixed with the chewing gum are adsorbed thereon.

These microgranules are then coated with the usual excipients and are then mixed with the gums. The technology used and some examples of the application thereof are given by way of non-limiting information:

A. Sugary microgranules of 850 microns diameter were introduced into a vessel provided with automatic spraying equipment and a system for blowing in hot air at 40°/80° C. and for recovering the blown air. If the formula requires it, the granules may be moistened with suitable flavouring essences before enlargement with syrup.

B. A syrup, possibly suitably flavoured, containing the micronized drug in suspension, was prepared (the mean quantities of drug which can be dispersed vary between 1 and 15% by weight of the syrup).

C. The granules were enlarged, care being taken to sift them frequently to prevent lumps and accumulations.

D. When all of the syrup had been absorbed by the granules, they were weighed to check how much of the drug had actually been absorbed, in order to determine the theoretical strength.

E. After the vessel had been carefully washed, the finished microgranules were coated therein with a solution of hydroxypropylmethyl cellulose in alcohol or with other lacquers suitable for rendering the granules Bore or less gastro-resistant, for example, lacquers based on methyl cellulose, acetyl cellulose, cellulose acetophthalate, etc.

| 10. BENZYDAMINE - gum tablets containing 3.0 mg of benzimidamine hydrochloride | |
|---|---|
| Lemery gum | 233.0 mg |
| Nostic gum | 233.0 mg |
| Sorbitol | 593.0 mg |
| Menthol | 17.0 mg |
| Essential oil of peppermint L | 7.35 mg |
| Glycerol | 21.0 mg |
| Aspartame | 4.3 mg |
| Sucrose | 243.0 mg |
| Starch | 91.0 mg |
| Magnesium stearate | 12.0 mg |
| Precipitated silica | 5.0 mg |
| Mint flavouring | 6.0 mg |
| Lemon flavouring | 7.0 mg |
| Anethole | 1.0 mg |
| Peppermint | 5.0 mg |
| Sweet mint | 3.0 mg |

| 11. NIMESULIDE - A 1.55 g gum tablet containing 50 mg of Nimesulide | |
|---|---|
| Sorbitol | 458 mg |
| Gum base | 439 mg |
| Sucrose | 260 mg |
| Sugary microspheres 850 mu | 180 mg |
| Orange flavouring | 55.6 mg |
| Citric acid | 27 mg |
| Hydroxypropylmethyl cellulose | 23 mg |
| Glycerol | 18 mg |
| Rice starch | 10 mg |
| Magnesium stearate | 10 mg |
| Polyethylene glycol | 7 mg |
| Aspartame | 5.2 mg |
| Titanium dioxide | 5 mg |
| Yellow colouring E102 | 2 mg |
| Red colouring E124 | 0.2 mg |

All of these examples should be considered purely as non-limiting examples, since the technology described can be applied without distinction to all pharmaceutically active ingredients with good absorption results. In fact the technology of the present invention enables the active ingredient to be modulated better and more conveniently with the use of the coating method made available by the pharmaceutical prior art for microencapsulation.

The fact that it is possible to regulate the mixing ratio between the active ingredient for immediate release and the active ingredient for slow release, combined with the particular lacquering system, simultaneously satisfies and reconciles several requirements, that is, taste and palatability, compliance by the patient and improved plasmatic and haematic absorption of the drug.

We claim:

1. Chewing gum tablet comprising:
    a mixture of a chewing gum base and sugary microgranules;
    a component adsorbed onto said sugary microgranules selected from the group consisting of an additive agent and an active ingredient; and
    a lacquer coating on the tablet selected from the group consisting of pharmaceutically acceptable celluloses and polyethylene glycols.

2. Chewing gum tablet according to claim 1, wherein said additive agent is a flavoring agent.

3. Chewing gum tablet according to claim 1, wherein said at least one active ingredient is in form of microencapsulated or otherwise delayed release coated particles.

4. Chewing gum tablet according to claim 1, wherein the cellulose is selected are selected from the group consisting of hydroxypropylmethyl cellulose, hydroxypropyl cellulose, methyl cellulose, ethyl cellulose, cellulose acetophthalate, carboxymethyl cellulose, hydroxyethyl cellulose, methylhydroxyethyl cellulose and methylhydroxypropyl cellulose phthalate.

5. Chewing gum tablet according to claim 1, wherein the polyethylene glycol is selected from the group consisting of polyethylene glycol 6000 and polyethylene glycol 400.

6. Chewing gum tablet according to claim 1, wherein the lacquer is supplemented with an additional component selected from the group consisting of colorings and dyes.

7. Chewing gum tablet according to claim 2, wherein some said particles of said active ingredient are microencapsulated and some are in free form in a predetermined ratio with regard to the patterns of initial delivery and of maintenance of the blood levels.

8. A method of preparing a tablet, comprising the steps of:
    a) freezing chewing gum in pellet form to a temperature of between $-20°$ C. and $-25°$ C. to form frozen gum;
    b) grinding said frozen gum to a particle size of between 60 and 190 mesh to form ground chewing gum;
    c) adding to said ground chewing gum sugary microgranules having adsorbed onto a surface thereof a component selected from the group consisting of an additive agent and au active ingredient to form a granular mixture;
    d) compressing said granular mixture to form tablets; and
    e) coating said tablets with a lacquer comprising a pharmaceutically acceptable celluloses or a polyethylene glycol in a solvent.

9. A method according to claim 8, wherein said ground chewing gum is mixed with at least one natural or synthetic sweetener in a ratio of 0.3–0.8 parts of gum per 0.6–0.2 parts of sweetener phase.

10. A method according to claim 9, wherein said additive agent is selected from the group consisting of a lubricant and a flavoring agent.

11. A method according to claim 10, wherein said active ingredient is added to the mixture of ground chewing gum, sweetener, lubricant and flavoring agent in the form of microencapsulated or otherwise delayed release coated particles.

12. A method according to claim 8, wherein said solvent is selected from the group consisting of water, an alcohol, acetone, and mixtures thereof.

13. A method according to claim 9, wherein said sweetener is selected from the group consisting of sugars, polyalcohols used as sweeteners, saccharin, acesulfame, aspartame and mixtures thereof.

14. A method according to claim 13, wherein the sugar is selected from the group consisting of dextrose, glucose, sucrose, invert sugar, fructose, mannose and maltose.

15. A method according to claim 13, wherein the polyalcohols are selected from the group consisting of sorbitol, mannitol, maltitol and xylitol.

16. A method according to claim 9, wherein the mixture of gum and sweetener is granulated moist and is dried on a fluid bed.

17. A method according to claim 8, wherein the mixture of said frozen chewing gum pellets and said sugary microgranules is granulated in moistened condition and dried on a fluid bed and then tablets are prepared by compression therefrom.

18. A method according to claim 10, wherein the lubricant is selected from the group consisting of alkali-metal or alkaline-earth metal stearates, stearic acid, hydrogenated vegetable oils and other lubricants used in the preparation of tablets for pharmaceutical use, and is added in an mount of between 0.2% and 2% by weight relative to the weight of the composition.

19. A method according to claim 10, wherein microgranular cellulose and/or precipitated silica are added together with said lubricant.

20. A method according to claim 19, wherein the microgranular cellulose is added in an amount of between 0.1% and 2% by weight.

21. A method according to claim 19, wherein the precipitated silica is added in quantities of between 0.05% and 1% by weight.

22. A method according to claim 8, wherein the flavoring agent is in liquid or powder form.

23. A method according to claim 8, wherein the lacquer is sprayed in a heated vessel with hot air.

24. A chewing gum composition comprising:
   a mixture of a chewing gum base and sugary microgranules;
   a component adsorbed onto said sugary microgranules selected from the group consisting of an additive agent and an active ingredient; and
   a lacquer coating on said microgranules selected from the group consisting of pharmaceutically acceptable cellusoses and polyethylene glycols.

25. Chewing gum composition according to claim 24, wherein said additive agent is a flavoring agent.

26. Chewing gum composition according to claim 24, wherein said at least one active ingredient is in form of microencapsulated or otherwise delayed release coated particles.

27. Chewing gum composition according to claim 24, wherein the cellulose is selected are selected from the group consisting of hydroxypropylmethyl cellulose, hydroxypropyl cellulose, methyl cellulose, ethyl cellulose, cellulose acetophthalate, carboxymethyl cellulose, hydroxyethyl cellulose, methylhydroxyethyl cellulose and methylhydroxypropyl cellulose phthalate.

28. Chewing gum composition according to claim 24, wherein the polyethylene glycol is selected from the group consisting of polyethylene glycol 6000 and polyethylene glycol 400.

29. Chewing gum composition according to claim 24, wherein the lacquer is supplemented with an additional component selected from the group consisting of colorings and dyes.

30. Chewing gum tablet according to claim 26, wherein some said particles of said active ingredient are microencapsulated and some are in free form in a predetermined ratio with regard to the patterns of initial delivery and of maintenance of the blood levels.

31. A method of preparing a chewing gum composition, comprising the steps of:
   a) providing sugary microgranules having adsorbed onto a surface thereof a component selected from the group consisting of an additive agent and an active ingredient;
   b) coating said sugary microgranules with a lacquer comprising a pharmaceutically acceptable celluloses or a polyethylene glycol in a solvent to form coated microgranules;
   c) mixing said coated microgranules with frozen ground chewing gum to form a chewing gum composition.

32. A method according to claim 31, wherein said chewing gum is frozen in pellet form to a temperature of between −20° C. and −25° C. and ground to a particle size of between 60 and 190 mesh.

33. A method according to claim 31, wherein said ground chewing gum is mixed with at least one natural or synthetic sweetener in a ratio of 0.3–0.8 parts of gum per 0.6–0.2 parts of sweetener phase.

34. A method according to claim 31, wherein said additive agent is selected from the group consisting of a lubricant and a flavoring agent.

35. A method according to claim 31, wherein said active ingredient is in the form of microencapsulated or otherwise delayed release coated particles.

36. A method according to claim 31, wherein said solvent is selected from the group consisting of water, an alcohol, acetone, and mixtures thereof.

37. A method according to claim 33, wherein said sweetener is selected from the group consisting of sugars, polyalcohols used as sweeteners, saccharin, acesulfame, aspartame and mixtures thereof.

38. A method according to claim 37, wherein the sugar is selected from the group consisting of dextrose, glucose, sucrose, invert sugar, fructose, mannose and maltose.

39. A method according to claim 37, wherein the polyalcohols are selected from the group consisting of sorbitol, mannitol, maltitol and xylitol.

40. A method according to claim 34, wherein the lubricant is selected from the group consisting of alkali-metal or alkaline-earth metal stearates, stearic acid, hydrogenated vegetable oils and other lubricants used in the preparation of tablets for pharmaceutical use, and is added in an mount of between 0.2% and 2% by weight relative to the weight of the composition.

41. A method according to claim 34, wherein the flavoring agent is in liquid or powder form.

42. A method according to claim 31, wherein the lacquer is sprayed in a heated vessel with hot air.

43. A method according to claim 31 and further including the step of compressing the chewing gum composition to form a tablet.

* * * * *